(12) United States Patent
McAndrew

(10) Patent No.: US 8,021,330 B2
(45) Date of Patent: Sep. 20, 2011

(54) BALLOON CATHETER FOR CROSSING A CHRONIC TOTAL OCCLUSION

(75) Inventor: Eamonn McAndrew, Knocknacarra (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 249 days.

(21) Appl. No.: 12/270,881

(22) Filed: Nov. 14, 2008

(65) Prior Publication Data
US 2010/0125244 A1    May 20, 2010

(51) Int. Cl.
  *A61M 29/00* (2006.01)
(52) U.S. Cl. ............. 604/98.01; 604/96.01; 604/97.01
(58) Field of Classification Search ........... 604/98.01, 604/97.01, 103.06, 103.08, 96.01, 523–525
See application file for complete search history.

(56) References Cited

U.S. PATENT DOCUMENTS

| | | | |
|---|---|---|---|
| 4,932,959 A * | 6/1990 | Horzewski et al. | 606/194 |
| 5,192,295 A | 3/1993 | Danforth et al. | |
| 5,265,622 A | 11/1993 | Barbere | |
| 5,273,052 A | 12/1993 | Kraus et al. | |
| 5,299,575 A | 4/1994 | Sandridge | |
| 5,324,259 A | 6/1994 | Taylor et al. | |
| 5,328,469 A | 7/1994 | Coletti | |
| 6,231,543 B1 * | 5/2001 | Hegde et al. | 604/96.01 |
| 6,251,084 B1 | 6/2001 | Coelho | |
| 6,488,688 B2 * | 12/2002 | Lim et al. | 606/108 |
| 6,602,224 B1 | 8/2003 | Simhambhatla | |
| 6,786,886 B2 * | 9/2004 | Miller et al. | 604/96.01 |
| 2003/0028234 A1 * | 2/2003 | Miller et al. | 623/1.11 |
| 2004/0173935 A1 | 9/2004 | Lim et al. | |
| 2005/0098914 A1 | 5/2005 | Varma et al. | |
| 2005/0118370 A1 | 6/2005 | Varma et al. | |

FOREIGN PATENT DOCUMENTS

| | | |
|---|---|---|
| EP | 0371486 | 6/1990 |
| EP | 0846472 | 6/1998 |

OTHER PUBLICATIONS

PCT/US2009/064229 International Search Report and Written Opinion mailed Feb. 15, 2010.

\* cited by examiner

*Primary Examiner* — Nicholas D Lucchesi
*Assistant Examiner* — Melissa A Snyder

(57) ABSTRACT

A balloon catheter is disclosed including a "no-fold" balloon at a distal end thereof that surrounds a distal portion of a guidewire shaft having a compliant shaft or tubular section for selectively gripping a guidewire there within. Upon introduction of inflation fluid at low pressure values, the compliant shaft section of the guidewire shaft is radially compressed to "lock" onto the guidewire while an outer diameter of the no-fold balloon remains unchanged. The simultaneous compression of the compliant shaft section against a guidewire located within the guidewire lumen and the filling of the balloon with inflation fluid without expanding the balloon provides a clinician with a conjoined balloon catheter and guidewire ensemble that together may be pushed through a tight stenosis such as a chronic total occlusion (CTO).

15 Claims, 5 Drawing Sheets

US 8,021,330 B2

BALLOON CATHETER FOR CROSSING A CHRONIC TOTAL OCCLUSION

FIELD OF THE INVENTION

The invention relates generally to a balloon catheter having improved pushability for crossing tight cardiovascular stenoses such as a chronic total occlusion.

BACKGROUND OF THE INVENTION

Cardiovascular disease, including atherosclerosis, is the leading cause of death in the United States. One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery, which may be accomplished by inflating a balloon of a balloon catheter within the narrowed lumen of the artery to dilate the vessel.

The anatomy of arteries varies widely from patient to patient. Often a patient's arteries are irregularly shaped, highly tortuous and very narrow. The tortuous configuration of the arteries may present difficulties to a clinician in advancement of the balloon catheter to a treatment site. In addition, in some instances, the extent to which the lumen is narrowed at the treatment site is so severe that the lumen is completely or nearly completely obstructed, which may be described as a total occlusion. If the occlusion has been established for a long period of time, the lesion may be referred to as a chronic total occlusion or CTO. Chronic total occlusions are often characterized by extensive plaque formation and typically include a fibrous cap surrounding softer plaque material. This fibrous cap may present a surface that is difficult to penetrate with a conventional medical guidewire such that one method of crossing a chronic total occlusion includes utilizing a stiffer guidewire to create a new channel through the occlusion.

Due to the fibrous cap of the total occlusion, a stiffer guidewire still may not be able to cross the occlusion and the distal end of the guidewire may buckle or prolapse within the vessel when force is applied. In addition, a clinician must take greater care to avoid perforation of the vessel wall when using a stiffer guidewire. Further, even if a stiffer guidewire can penetrate the proximal fibrous cap of the total occlusion, it may not be able to completely cross the occlusion due to multiple non-functional channels that often occur throughout the occlusion, which if entered by the guidewire lead to dead-end pathways and/or to the creation of false tracts within the occlusion and the problems attendant thereto.

Another challenge with the treatment of chronic total occlusions is that even after a guidewire successfully crosses the occlusion, the clinician may not be able to advance a dilatation balloon over the guidewire due to the fibrocalcific composition of the chronic total occlusion. In such situations, additional or alternative interventional devices may be needed to treat the occlusion further complicating the procedure. Accordingly, there exists a need in the art for improved devices and methods for treatment of a CTO.

BRIEF SUMMARY OF THE INVENTION

Embodiments hereof are directed to a balloon catheter having an inflation lumen, a balloon in fluid communication with the inflation lumen, and a guidewire shaft disposed within at least a distal portion of the inflation lumen. The guidewire shaft defines a guidewire lumen for receiving a guidewire therethrough and has a compliant shaft section that is radially compressible upon delivery of an inflation fluid at an actuation pressure through the inflation lumen. An outer diameter of the balloon remains unchanged during delivery of the inflation fluid at the actuation pressure. The simultaneous compression of the compliant shaft section against a guidewire located within the guidewire lumen and the filling of the balloon with inflation fluid without expanding the balloon provides a clinician with a conjoined balloon catheter and guidewire ensemble that together may be pushed through a tight stenosis, such as a chronic total occlusion (CTO).

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Figure 1:
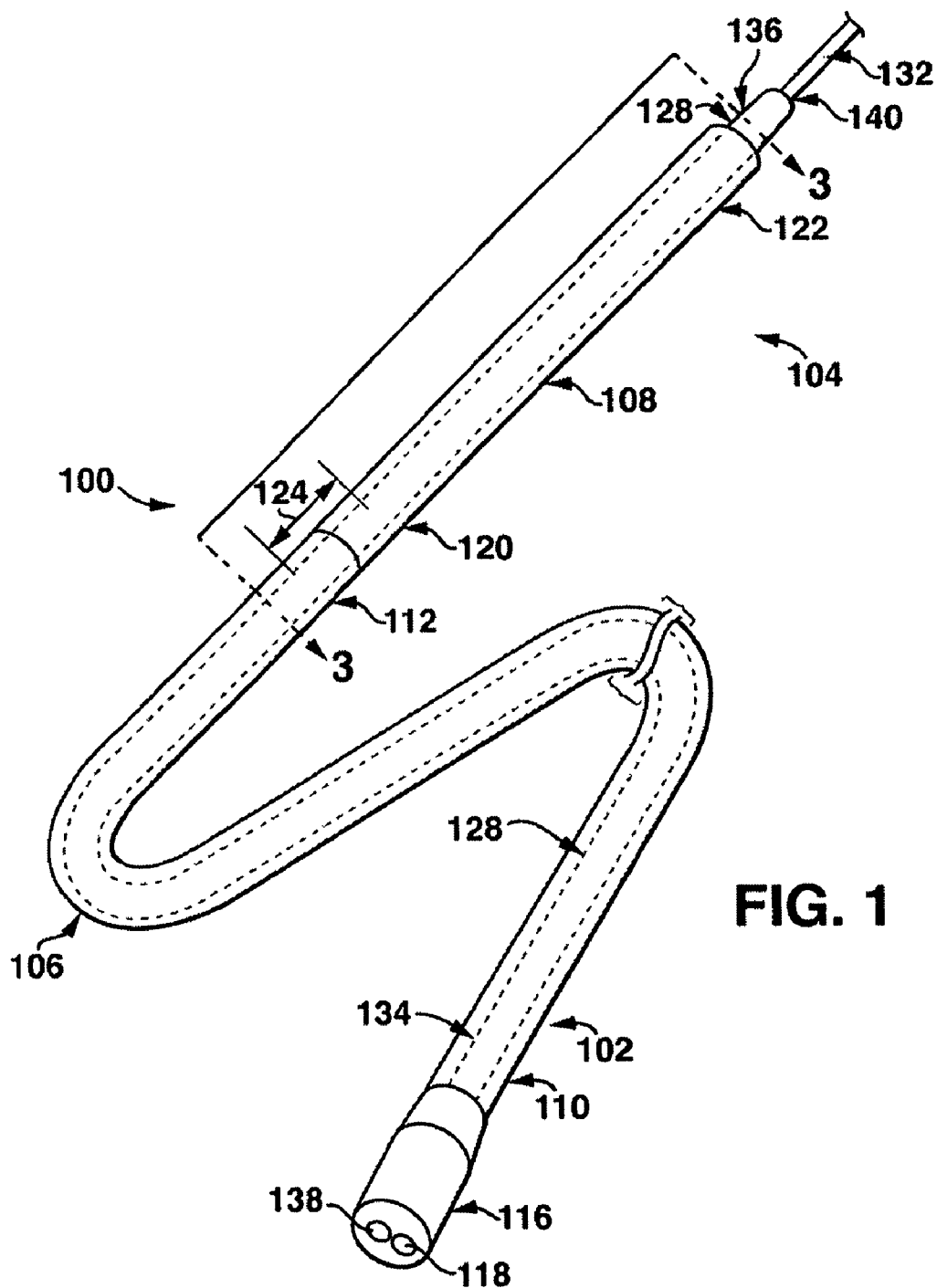
FIG. 1 is a side perspective view of a balloon catheter, wherein the balloon is in an unexpanded configuration, in accordance with an embodiment hereof.
Figure 2A:
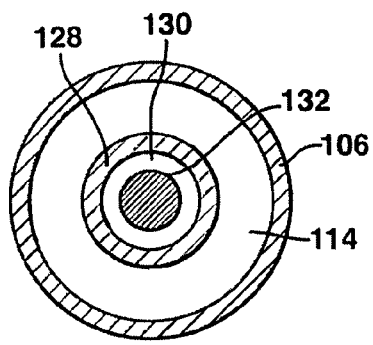
FIG. 2A is a cross-sectional view taken along line A-A of FIG. 2.
Figure 2:
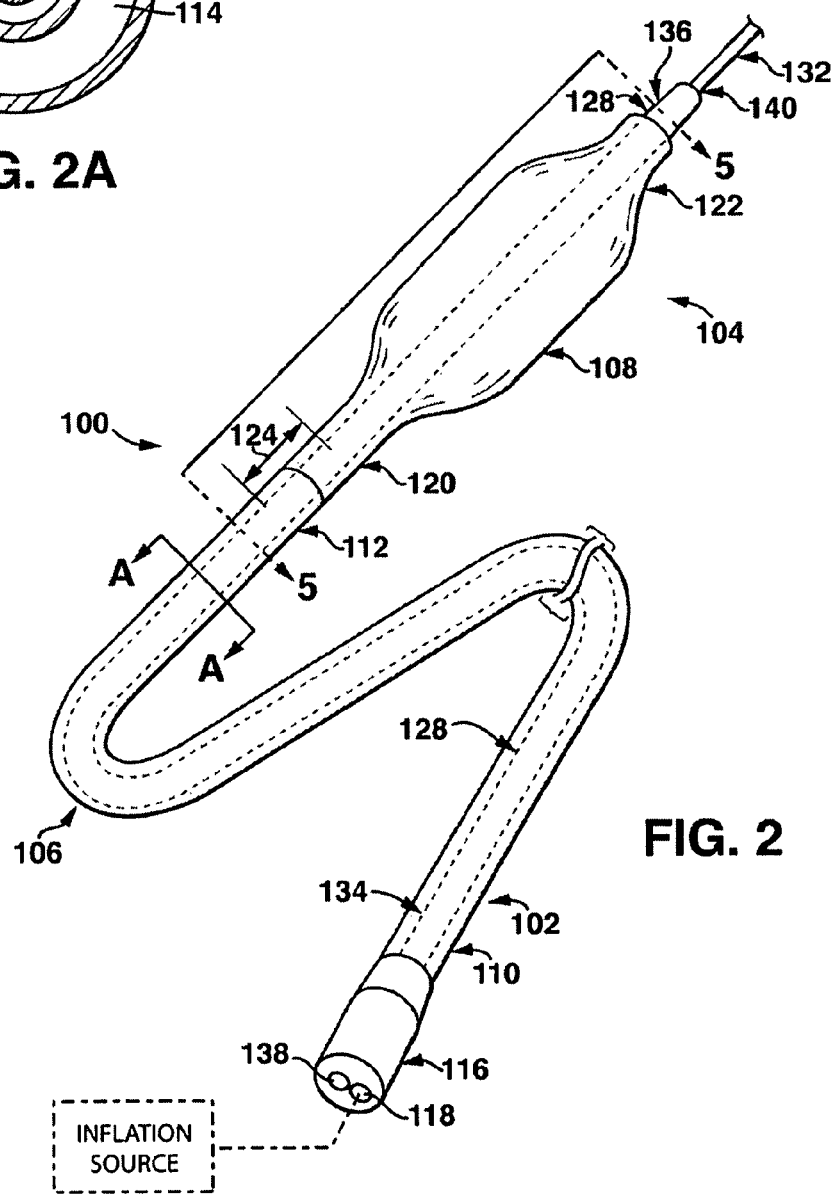
FIG. 2 is a side perspective view of the balloon catheter of FIG. 1, wherein the balloon is in an expanded configuration.

FIGS. 1, 2 and 2A depict a balloon catheter 100 according to an embodiment hereof. Balloon catheter 100 includes a proximal portion 102 that extends out of the patient and has a hub 116. Distal portion 104 of catheter 100 is positionable at a target location within the vasculature and includes an inflatable balloon 108, which is shown in an unexpanded or delivery configuration in FIG. 1 and in an expanded or inflated configuration in FIG. 2. In embodiments hereof, catheter 100 may be used in balloon angioplasty procedures, as well as may form the basis of a stent delivery system, a graft delivery system, and/or a drug delivery system.

In the embodiment shown in FIGS. 1, 2 and 2A, balloon catheter 100 has an over-the-wire (OTW) catheter configuration with an inner guidewire shaft 128 that defines a guidewire lumen 130 extending substantially the entire length of the catheter for accommodating a guidewire 132. More particularly, catheter 100 includes a tubular component or outer shaft 106 having a proximal end 110 coupled to hub 116 and a distal end 112 coupled to balloon 108. Guidewire shaft 128 has a proximal end 134 coupled to a proximal guidewire port 138 of hub 116 and a distal end 136 terminating distally of balloon 108 and defining a distal guidewire port 140. In an embodiment, guidewire shaft 128 may be a flexible tube of a polymeric material, such as, e.g., polyethylene tubing.

In the coaxial catheter construction of the illustrated embodiment, guidewire shaft 128 extends within outer shaft 106 such that an annular inflation lumen 114 is defined between an inner surface of outer shaft 106 and an outer surface of guidewire shaft 126. Other types of catheter construction are also amendable to the invention, such as, without limitation thereto, a catheter shaft formed by multi-lumen profile extrusion. Inflation lumen 114 extends between proximal and distal ends 110, 112 of outer catheter shaft 106 to allow inflation fluid received through an inflation port 118 of hub 116 to be delivered to balloon 108. As would be understood by one of ordinary skill in the art of balloon catheter design, hub 116 provides a luer hub or other type of fitting that may be connected to a source of inflation fluid and may be of another construction or configuration without departing from the scope of the present invention.

As will be explained in more detail below, balloon 108 is a "no-fold" or "zero-fold" balloon, which means that the balloon material is not folded prior to inflation but instead has a generally cylindrical or tubular shape in the unexpanded configuration shown in FIG. 1. An unexpanded no-fold balloon 108 generally has a reduced profile as compared with a more conventional balloon, which must be folded around the catheter in the unexpanded state during delivery, resulting in improved crossability and trackability. The term "crossability" refers to the ability of a balloon catheter to insert the deflated balloon into a targeted vessel narrowing to a generally axially centered position for performing angioplasty or balloon dilatation. The term "trackability" refers to the ability of a catheter to be advanced along a curved path, e.g. to "track" a catheter through tortuous blood vessels over a pre-placed guidewire. In the unexpanded configuration of FIG. 1, balloon 108 has an outer diameter that is uniform along the full length of balloon 108. In an embodiment, the unexpanded outer diameter of balloon 108 is approximately 0.6 mm. When radially expanded to the configuration depicted in FIG. 2, balloon 108 assumes a more conventional dilatation balloon shape having an inflated outer diameter that enlarges a lumen of the affected artery. In an embodiment, the expanded outer diameter of balloon 108 may be between approximately 1 mm to 3 mm. In some instances, the initial inflation of no-fold balloon 108 to its nominal diameter causes plastic deformation to occur in the balloon material such that, upon deflation of balloon 108, wings or folds of balloon material are formed.

Balloon 108 includes a proximal neck 120 and a distal neck 122. In the embodiment shown in FIG. 3, which is an enlarged longitudinal sectional view of distal portion 104 of catheter 100 taken along line 3-3 of FIG. 1, proximal neck 120 of balloon 108 is placed inside and joined to distal end 112 of outer shaft 106 in a joint transition area 124. Encircling outer shaft distal end 112 over balloon proximal neck 120 accommodates the uniform cylindrical shape of unexpanded no-fold balloon 108. Further, with proximal neck 120 of balloon 108 secured within outer shaft 106, a smaller outer diameter at joint transition area 124 is achieved thus providing catheter 100 with a reduced profile. Further details regarding the joint between no-fold balloon 108 and outer shaft 106 are described in U.S. patent application Ser. No. 12/049,687 to McAndrew et al. entitled "Outer Catheter Shaft to Balloon Joint" filed Mar. 18, 2008, herein incorporated by reference in its entirety. Distal neck 122 of balloon 108 encircles and is joined to guidewire shaft 128 at joint 142. Proximal and distal necks 120, 122 of balloon 108 may be joined to outer catheter shaft 106 and guidewire shaft 128, respectively, in any conventional manner known to one of skill in the art of balloon catheter construction, such as by laser welding, adhesives, heat fusing, or ultrasonic welding. In another embodiment where no-fold balloon 108 has an inner diameter that is greater than or substantially equal to an outer diameter of outer shaft 106, proximal neck 120 may be overlapped and secured around outer shaft distal end 112 by any of the aforementioned methods.

Figure 3:
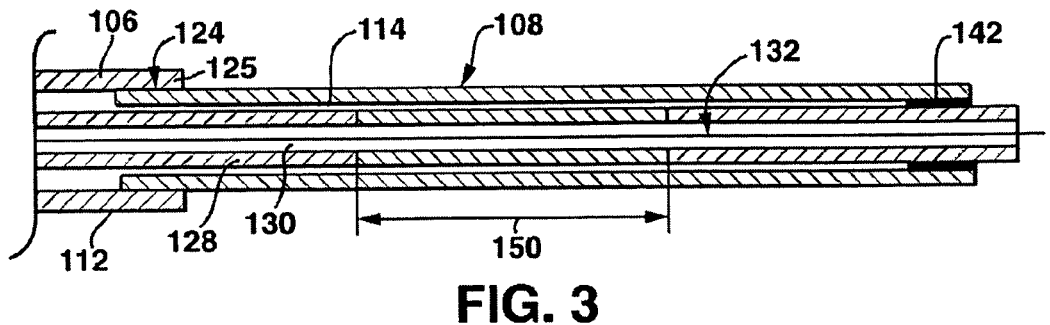
FIG. 3 is a longitudinal sectional view taken along line 3-3 of FIG. 1, wherein the balloon is in the unexpanded or delivery configuration and the compliant shaft section of the guidewire shaft is not compressed against the guidewire.
Figure 4:
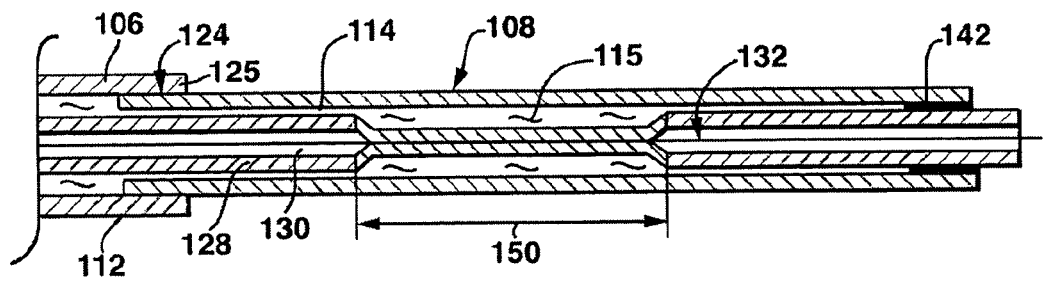
FIG. 4 is a sectional view taken along line 3-3 of FIG. 1, wherein the balloon is in the unexpanded or delivery configuration and the compliant shaft section of the guidewire shaft is compressed against the guidewire.
Figure 5:
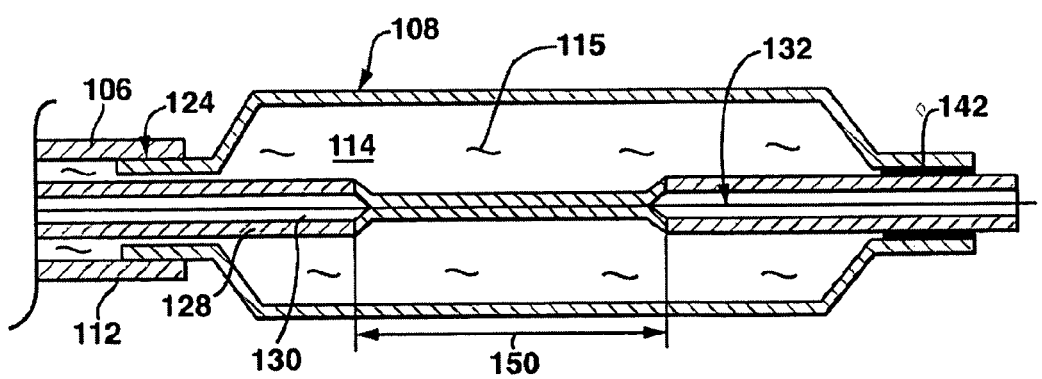
FIG. 5 is a sectional view taken along line 5-5 of FIG. 2, wherein the balloon is in its fully inflated or fully expanded configuration and the compliant shaft section of the guidewire shaft is compressed against the guidewire.

Referring now to FIGS. 3-5, guidewire shaft 128 includes a compliant shaft or tubular section 150 that is situated within an interior of balloon 108 such that an outer surface thereof may be contacted by inflation fluid 115. In various embodiments, compliant shaft section 150 may be between 10 mm-20 mm in length. As shown in FIG. 4, when balloon 108 receives inflation fluid 115 at a predetermined actuation pressure value PA, compliant shaft section 150 is constructed to be radially compressed into a frictional engagement with or substantially "locked" to a guidewire 132 inserted within guidewire lumen 130 of guidewire shaft 128. Guidewire 132 is shown somewhat schematically in FIGS. 3-5 as only a single line for simplicity of illustration. In one embodiment, the predetermined actuation pressure PA is between 2 and 5 atmospheres (atm). At the actuation pressure PA, no-fold balloon 108 is constructed to remain unexpanded such that the outer diameter of balloon 118 remains unchanged. When compliant shaft section 150 is locked down onto guidewire 132, conjoined balloon catheter 100 and guidewire 132 have an increased ability as an ensemble to cross the lesion when the clinician pushes both the guidewire and the balloon catheter. In addition, with inflation fluid 115 present at the actuation pressure PA within unexpanded balloon 108, balloon 108 has increased stiffness that is additive to the overall pushability of conjoined balloon catheter 100 and guidewire 132 for crossing the lesion. The term "pushability" refers to the ability of a catheter distal tip to be pushed against resistance without having the catheter shaft buckle, e.g., longitudinal stiffness.

Once catheter 100 has successfully crossed the lesion, additional inflation fluid 115 is introduced to increase the inflation fluid pressure within balloon 108 to a predetermined expansion pressure PE that will cause balloon 108 to begin to radially expand to its fully inflated configuration shown in FIG. 5. In one embodiment, the predetermined expansion pressure PE at which balloon 108 begins to radially expand is between 6 atm and 15 atm. Upon removal of inflation fluid 115 with the attendant drop in inflation fluid pressure below PA, balloon 108 will deflate and compliant shaft section 150 will return to its original, non-compressed configuration shown in FIG. 3

The materials, dimensions and processing of compliant shaft section 150 and balloon 108 are selected to provide compressibility of section 150 into frictional engagement with guidewire 132 at an inflation fluid pressure of at least predetermined actuation pressure PA, where PA is always less than predetermined expansion pressure PE, i.e., the inflation fluid pressure at which balloon 108 begins to inflate or, stated another way, first experiences an increase in outer diameter. At any inflation fluid pressures above predetermined actuation pressure PA, compliant shaft section 150 will remain substantially locked to guidewire 132.

In one embodiment depicted in FIGS. 3-5, compliant shaft section 150 may be constructed to have a different stiffness than the remainder of guidewire shaft 128. More particularly, compliant shaft section 150 may be formed from a first material having a first stiffness that permits the compliant shaft section to be compressed at the predetermined actuation pressure PA. Stiffness refers to the resistance of an elastic body to deflection or deformation by an applied force. Accordingly, the remainder of the guidewire shaft 128 may be formed from a second material having a second stiffness that is greater than the first stiffness, such that the remainder of guidewire shaft does not radially collapse or compress at any pressure of inflation fluid 115. Thus, when the pressure applied by inflation fluid 115 around the exterior of compliant shaft section 150 of guidewire shaft 128 is equal to or exceeds the predetermined actuation pressure PA, the less stiff compliant shaft section 150 will be radially compressed and consequently locked against guidewire 132.

Compliant shaft section 150 and the remainder of guidewire shaft 128 are sealingly coupled together to form a continuous guidewire shaft 128. Any suitable coupling mechanisms or methods known to one of skill in the art of catheter construction may be employed for coupling compliant shaft section 150 to the remainder of the guidewire shaft 128 such as by laser welding, adhesives, heat fusing, or ultrasonic welding. In an embodiment, the first, less stiff material of compliant shaft section 150 may be PEBAX® 6333 polyethylene block amide (PEBA) copolymer from Arkema, Inc. of Philadelphia, Pa., and the second material forming the remainder of guidewire shaft 128 may include polyethylene with or without a PEBA outer layer for bondability. In another embodiment, compliant shaft section 150 may be made of the same material as the remainder of guidewire shaft 128. To provide relatively less stiffness, compliant shaft section 150 has a wall thickness less than the wall thickness of the remainder of guidewire shaft 128, as may be achieved e.g., by making two different extrusions of the same material.

The location of compliant shaft section 150 is not limited to the position illustrated in FIG. 3, such that in other embodiments hereof compliant shaft section 150 may be positioned proximal or distal of balloon 108 as long as compliant shaft section 150 is actuatable by an inflation fluid 115 as described above.

In another embodiment, manufacturing or processing steps may be employed in order to alter the stiffness, i.e., resistance to compression of a portion of the guidewire shaft material. More particularly, compliant shaft section 150 may be an integral portion of guidewire shaft 128, such that guidewire shaft 128 is a unitary structure from proximal end 134 to distal end 136 that is initially formed from a single material having a first stiffness. A second stiffness less than the first stiffness, in compliant shaft section 150 is then achieved via a processing step, such as necking or thinning of the shaft wall in order to reduce the stiffness of compliant shaft section 150 with respect to the remainder of guidewire shaft 128. In an embodiment suitable for necking or thinning, guidewire shaft 128 may be formed from an integral, seamless tube of a thermoplastic, such as PEBA or polyethylene with or without a PEBA outer layer.

As previously mentioned, balloon 108 is constructed to remain unexpanded at the predetermined actuation pressure PA such that the outer diameter of the no-fold balloon remains unchanged when compliant shaft section 150 of guidewire shaft 128 locks onto a guidewire. In an embodiment to achieve a resistance to expansion, balloon 108 may be constructed with a relatively greater wall thickness than a conventional balloon, with the greater wall thickness being consistent along the entire length of the balloon. Such a relatively thicker wall prevents balloon 108 from having any expansion until the inflation fluid pressure reaches predetermined expansion pressure PE. In one embodiment, the wall thickness is approximately 0.000775 inches. Balloon 108 may be formed from any material that is relatively elastic and deformable. Non-exhaustive examples of materials for balloon 108 include polymers such as polyethylene, PEBA, polyethylene terephthalate (PET), polyamide, and polyurethane. Further details regarding no-fold balloon technology are described in U.S. patent application Ser. No. 12/049,687, previously incorporated by reference in its entirety. In an embodiment, balloon catheter 100 may include a balloon 108 such as the 1.25 mm nominal diameter balloon with "Zero-Fold Technology", which is available on the SPRINTER® Legend Balloon Catheter manufactured by Medtronic, Inc. of Minneapolis, MINN. Zero-Fold Technology includes a balloon featuring no wings or folded or wrapped material and no balloon shoulders thus facilitating crossing tightly occluded lesions.

Figure 6:
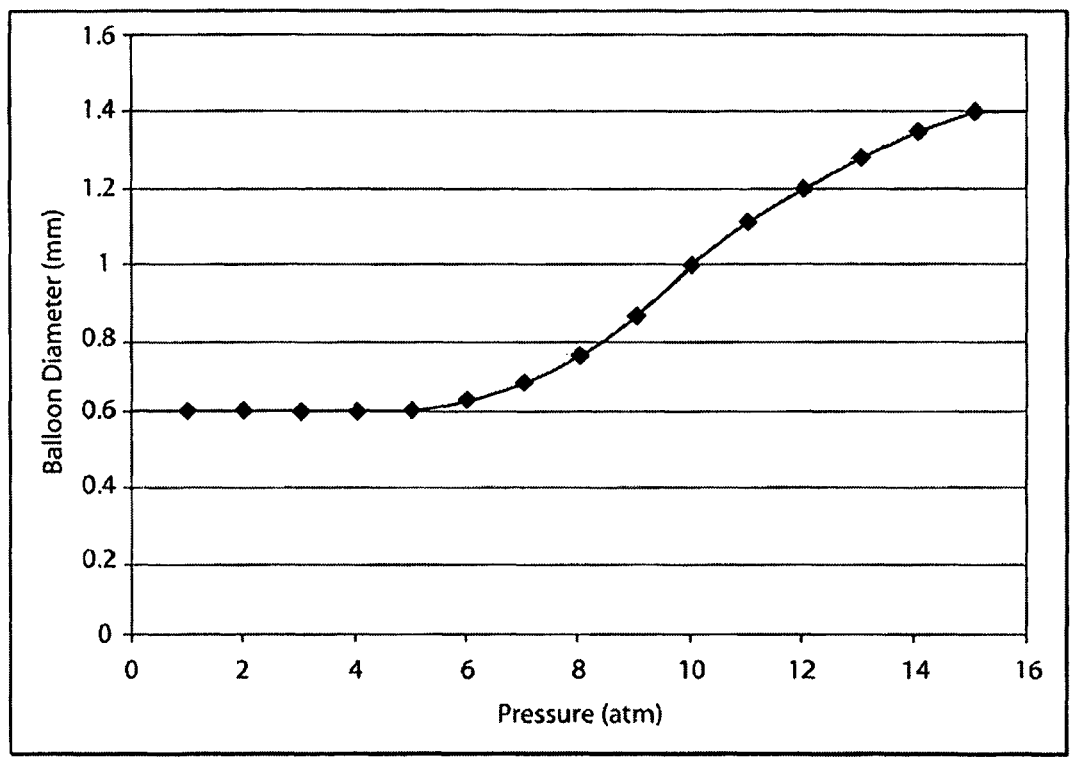
FIG. 6 is a compliance curve for a balloon according to an embodiment hereof.

FIG. 6 is an exemplary compliance curve for balloon 108 according to an embodiment hereof. As shown in FIG. 6, the outer diameter of balloon 108 remains unchanged at 0.60 mm during inflation fluid pressure values of zero to 5 atm. Thus, when the predetermined actuation pressure PA for collapsing compliant shaft section 150 of guidewire shaft 128 is between 1 atm and 5 atm, balloon 108 receives inflation fluid under pressure but remains unexpanded. When the inflation fluid is pressurized to the predetermined expansion pressure PE of 6 atm, balloon 108 begins to radially expand, or inflate. As the inflation fluid pressure increases to 15 atm, balloon 108 reaches its fully expanded configuration having an outer diameter of approximately 1.40 mm.

Outer shaft 106 may be formed of a polymeric material, non-exhaustive examples of which include polyethylene, PEBA, polyamide and/or combinations thereof, either blended or co-extruded. Optionally, outer shaft 106 or some portion thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like. In one embodiment, for example, at least a proximal portion of outer catheter shaft 106 may be formed from a reinforced polymeric tube.

In another embodiment, catheter 100 may be modified to be of a rapid exchange (RX) catheter configuration without departing from the scope of the present invention such that guidewire shaft 128 extends within only distal portion 104. In such an embodiment, a proximal portion of outer catheter shaft 106 may include a metal hypotube with a guidewire transition area having a proximal guidewire port being positioned proximal of balloon 108 approximately 20 cm to 25 cm. Guidewire shaft 128, which in an embodiment may be of a polymeric tubing, would then extend within only distal portion 104 of catheter 100 surrounded by a distal portion of inflation lumen 114 and compliant shaft section 150 of guidewire shaft 128 would be positioned within balloon 108, or just proximal or distal thereof, so as to be in contact with and actuatable by an inflation fluid as described above with reference to the OTW embodiment.

Figure 7:
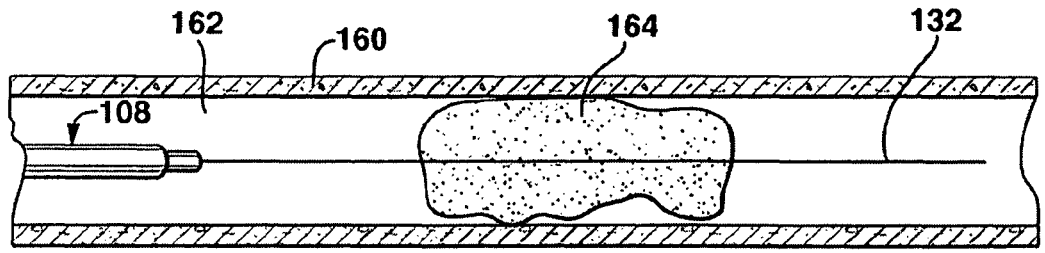
FIGS. 7-10 illustrate the steps of a method of crossing a chronic total occlusion according to an embodiment hereof.

FIGS. 7-10 illustrate the steps of a method of crossing a chronic total occlusion according to an embodiment hereof. Although described in relation to crossing a chronic total occlusion, it should be understood that the methods and apparatus described herein may be used for crossing any tight stenoses and are not limited to total occlusions. Further, although described as advancing a balloon catheter over a previously positioned guidewire, it should be understood that the balloon catheter and guidewire may be simultaneously advanced to and through the target lesion. Typically, a guiding catheter is first inserted through an incision (not shown) and into a femoral artery of a patient. A guidewire 132 is typically pre-loaded into catheter 100 and the ensemble is then inserted into the guiding catheter and maneuvered through the vasculature to a treatment site, which in this instance is shown as a chronic total occlusion (CTO) 164 within lumen 162 of vessel 160. In the method shown, guidewire 132 is advanced and navigated alone through occlusion 164. As shown in FIG. 7, catheter 100 is positioned by a clinician such that the distal end of catheter 100 is proximal of occlusion 164. Inflation fluid is then introduced into catheter 100 at the predetermined actuation pressure PA such that compliant shaft section 150 of guidewire shaft 128 is compressed against guidewire 132 (see also FIG. 4). In one embodiment, the predetermined actuation pressure PA is less than 6 atm, and in another embodiment is between 2 atm and 3 atm. Balloon 108 receives inflation fluid but remains unexpanded such that the outer diameter of the no-fold balloon remains unchanged.

Figure 8:
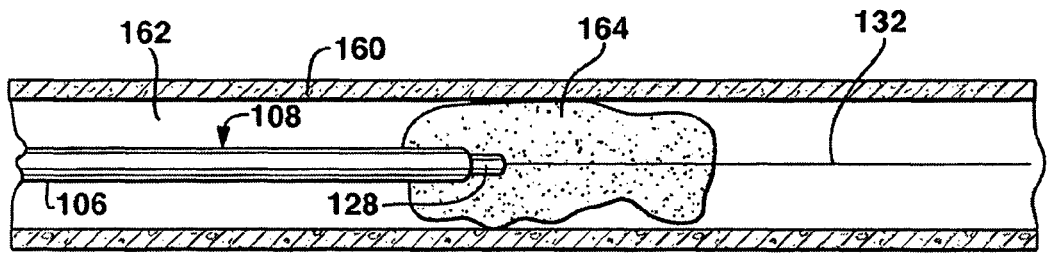
Figure 9:
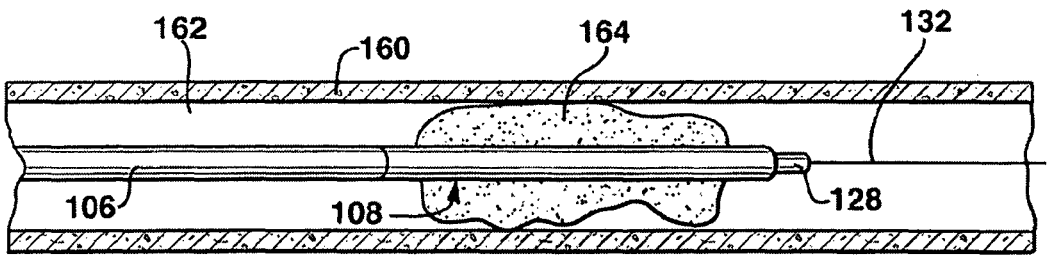

Referring to FIG. 8, with compliant shaft section 150 locked onto guidewire 132 and balloon 108 stiffened, but not expanded, by inflation fluid within the balloon at a pressure less than predetermined expansion pressure PE, the conjoined catheter 100 and guidewire 132 ensemble is pushed until the distal end of catheter 100 is pushed into occlusion 164. In another embodiment, a channel (not shown) may be previously created within occlusion 164 by a ROTABLATOR® rotational atherectomy system, manufactured by Boston Scientific Corporation, in order to facilitate advancement of the distal end of catheter 100 within the CTO. Due to the frictional engagement of compliant shaft section 150 with guidewire 132, the guidewire/balloon catheter ensemble provides enhanced pushability for crossing occlusion 164. In addition, as mentioned above, unexpanded balloon 108 contains pressurized inflation fluid which makes balloon 108 stiffer and improves pushability thereof across the lesion. Catheter 100 and guidewire 132 are advanced as a unit until balloon 108 successfully "crosses" occlusion 164 to become longitudinally centered there within, as shown in FIG. 9.

Figure 10:
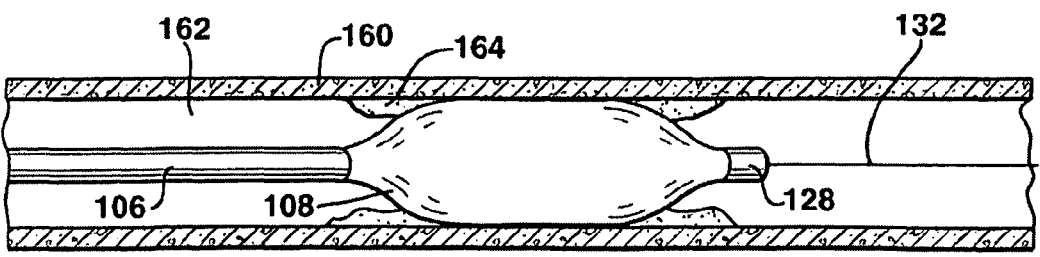

Once balloon 108 is positioned within the lesion, additional inflation fluid is introduced such that the pressure in the inflation fluid is increased to the predetermined expansion pressure PE so that balloon 108 begins to radially expand. In one embodiment, the predetermined expansion pressure PE is 6 atm and in another embodiment PE is above 6 atm and may be, more particularly, between 7 atm and 10 atm. As the inflation fluid pressure is increased above the predetermined expansion pressure PE, balloon 108 will radially expand to its fully-inflated configuration to dilate occlusion 164 and thereby enlarge lumen 162 of vessel 160 at the lesion, as shown in FIG. 10 (see also FIG. 5). In an embodiment, as the inflation fluid pressure increases to between 12 atm and 15 atm, balloon 108 will reach an expanded outer diameter between 1.20 mm and 1.40 mm. Once the angioplasty procedure is completed, inflation fluid is withdrawn in order to deflate balloon 108. Since the pressure in the inflation fluid will fall below actuation pressure PA when balloon. 108 is deflated, compliant shaft section. 150 will resume its original, non-compressed configuration, thus releasing guidewire 132. Upon deflation, balloon 108 may form wings or folds of material around catheter 100 and catheter 100 may be retracted from the patient. If desired, another interventional catheter such as a balloon catheter having a larger balloon or a stent delivery system may be delivered over indwelling guidewire 132 to occlusion 164 in order to perform additional therapeutic procedures.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A balloon catheter comprising:
   a tubular component defining an inflation lumen in fluid communication with a source of inflation fluid;
   a balloon having an interior in fluid communication with the source of inflation fluid via the inflation lumen of the tubular component; and
   a guidewire shaft disposed within at least a distal portion of the catheter, the guidewire shaft defining a lumen sized to slidably receive a guidewire and having a compliant shaft section that is radially compressible against the guidewire when inflation fluid received within the inflation lumen of the tubular component is pressurized to at least an actuation pressure PA, wherein the balloon surrounds a portion of the guidewire shaft and remains in a delivery configuration when the inflation fluid is at the actuation pressure PA, wherein in the delivery configuration the balloon is unexpanded.

2. The balloon catheter of claim 1, wherein in the delivery configuration the balloon has no wings and no material folded or wrapped around the catheter.

3. The balloon catheter of claim 1, wherein the actuation pressure PA is less than 6 atm.

4. The balloon catheter of claim 3, wherein the actuation pressure PA is between 2 atm and 5 atm.

5. The balloon catheter of claim 3, wherein the balloon begins to radially expand when the inflation fluid within the inflation lumen of the tubular component is pressurized to an expansion pressure PE that is greater than the actuation pressure PA.

6. The balloon catheter of claim 5, wherein the expansion pressure PE is equal to or greater than 6 atm.

7. The balloon catheter of claim 1, wherein the compliant shaft section of the guidewire shaft is positioned within the interior of the balloon.

8. The balloon catheter of claim 1, wherein the compliant shaft section is constructed from a first material and the guidewire shaft is constructed from a second material stiffer than the first material.

9. The balloon catheter of claim 1, wherein the balloon is an angioplasty balloon.

10. A balloon catheter coupled to an inflation fluid source, the catheter comprising:
  an elongate shaft defining an inflation lumen that is in fluid communication with the inflation fluid source;
  a flexible tube at least partially disposed within a distal portion of the elongate shaft, the tube defining a lumen sized to receive a guidewire and including a compliant tubular section having an outer surface contactable by inflation fluid delivered through the inflation lumen of the elongate shaft, the compliant tubular section being radially compressible against a guidewire disposed therethrough when acted on by pressurized inflation fluid at an actuation pressure PA; and
  a balloon surrounding a portion of the tube and having an interior in fluid communication with the inflation lumen of the elongate shaft, wherein the balloon remains in a delivery configuration at an inflation fluid pressure of less than or equal to the actuation pressure PA, wherein in the delivery configuration the balloon is unexpanded.

11. The balloon catheter of claim 10, wherein in the delivery configuration the balloon has no wings and no material folded or wrapped around the catheter, 12. The balloon catheter of claim 10, wherein the actuation pressure PA is less than 6 atm.

13. The balloon catheter of claim 12, wherein the actuation pressure PA is between 2 atm and 5 atm.

14. The balloon catheter of claim 12, wherein the balloon begins to expand when the inflation fluid pressure reaches an expansion pressure PE of equal to or greater than 6atm.

15. The balloon catheter of claim 10, wherein the compliant tubular section of the tube is positioned within the interior of the balloon.

\* \* \* \* \*